US007582727B1

(12) United States Patent
Krishna et al.

(10) Patent No.: US 7,582,727 B1
(45) Date of Patent: *Sep. 1, 2009

(54) PHARMACEUTICAL FORMULATIONS OF BIVALIRUDIN AND PROCESSES OF MAKING THE SAME

(75) Inventors: Gopal Krishna, Parsippany, NJ (US); Gary Musso, Parsippany, NJ (US)

(73) Assignee: The Medicinces Company, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/180,553

(22) Filed: Jul. 27, 2008

(51) Int. Cl.
*A61K 38/55* (2006.01)
*C07K 7/08* (2006.01)
*C07K 7/64* (2006.01)
*C07K 1/00* (2006.01)
*C07K 1/04* (2006.01)
*C07K 14/00* (2006.01)

(52) U.S. Cl. .................. 530/326; 530/324; 530/333; 530/334; 530/335; 514/13

(58) Field of Classification Search .............. None
See application file for complete search history.

(56) References Cited

U.S. PATENT DOCUMENTS

| 5,196,404 | A | 3/1993 | Maraganore et al. |
|---|---|---|---|
| 5,240,913 | A | 8/1993 | Maraganore et al. |
| 5,425,936 | A | 6/1995 | Maraganore et al. |
| 5,433,940 | A | 7/1995 | Maraganore et al. |
| 5,691,311 | A | 11/1997 | Maraganore et al. |
| 5,786,330 | A | 7/1998 | Fauchere et al. |
| 6,274,553 | B1 | 8/2001 | Furuya et al. |
| 7,390,788 | B2 | 6/2008 | Pert et al. |
| 7,425,542 | B2 | 9/2008 | Maggio |
| 2007/0093423 | A1 | 4/2007 | Tovi et al. |
| 2007/0116729 | A1 | 5/2007 | Palepu |
| 2008/0051558 | A1 | 2/2008 | Zhou |
| 2008/0268032 | A1 | 10/2008 | Maggio |
| 2008/0287650 | A1 | 11/2008 | Tovi et al. |
| 2009/0062511 | A1 | 3/2009 | Palle et al. |

FOREIGN PATENT DOCUMENTS

| WO | 2006/045503 | 5/2006 |
|---|---|---|
| WO | WO 2007149096 | 12/2007 |

OTHER PUBLICATIONS

EMEA Publication. "Scientific Discussion", 2004, p. 1-32 (www.emea.europa.eu/humandocs/PDFs/EPAR/angiox/103304en6.pdf).
W.M. Davis, M.C. Vinson, *Drug Topics* 2001, 145: 5, p. 89.
M. Staples, *Pharm. Res.* 1992, 9:10, Suppl., S79.
U.S. Appl. No. 12/180,550, filed Jul. 27, 2008, Krishna et al.
U.S. Appl. No. 12/180,551, filed Jul. 27, 2008, Krishna et al.
Amsberry et al., "Compatibility and Stability of Bivalirudin in IV Admixtures" : http://www.aapsj.org/abstracts/AM_1999/923.htm. (1999).
Bam Biotech Abstract, titled "Bivalirudin" : http://www.bambio.com/show.asp?id=107. (Sep. 27, 2006).
Angiomax® U.S. Prescribing Information, Dec. 6, 2005.

*Primary Examiner*—Cecilia Tsang
*Assistant Examiner*—Julie Ha
(74) *Attorney, Agent, or Firm*—Frommer Lawrence & Haug LLP; Sandra Kuzmich; Russell A. Garman

(57) ABSTRACT

Pharmaceutical batch(es) or pharmaceutical formulation(s) comprising bivalirudin as the active ingredient, and a method of preparing the pharmaceutical batch(es) or pharmaceutical formulation(s). The pharmaceutical batch(es) or pharmaceutical formulation(s) may have a maximum impurity level of $Asp^9$-bivalirudin that does not exceed about 0.6%. Also, the pharmaceutical batch(es) or pharmaceutical formulation(s) may have a reconstitution time that does not exceed about 42 seconds. The method of preparing the pharmaceutical batch(es) or pharmaceutical formulation(s) may comprise dissolving bivalirudin in a solvent to form a first solution, efficiently mixing a pH-adjusting solution with the first solution to form a second solution in which the pH-adjusting solution may comprise a pH-adjusting solution solvent, and removing the solvent and the pH-adjusting solution solvent from the second solution.

20 Claims, No Drawings

SEQUENCE LISTING

<160> NUMBER OF SEQ ID NOS: 3

<210> SEQ ID NO 1
<211> LENGTH: 20

```
<212> TYPE: PRT
<213> ORGANISM: Artificial Sequence
<220> FEATURE:
<223> OTHER INFORMATION: Modified protein from Hirudo medicinalis
<220> FEATURE:
<221> NAME/KEY: MISC_FEATURE
<222> LOCATION: (1)..(1)
<223> OTHER INFORMATION: Residue is a D-isomer

<400> SEQUENCE: 1

Phe Pro Arg Pro Gly Gly Gly Gly Asn Gly Asp Phe Glu Glu Ile Pro
1               5                   10                  15

Glu Glu Tyr Leu
            20

<210> SEQ ID NO 2
<211> LENGTH: 20
<212> TYPE: PRT
<213> ORGANISM: Artificial Sequence
<220> FEATURE:
<223> OTHER INFORMATION: Modified protein from Hirudo medicinalis
<220> FEATURE:
<221> NAME/KEY: MISC_FEATURE
<222> LOCATION: (1)..(1)
<223> OTHER INFORMATION: Residue is a D-isomer

<400> SEQUENCE: 2

Phe Pro Arg Pro Gly Gly Gly Gly Asp Gly Asp Phe Glu Glu Ile Pro
1               5                   10                  15

Glu Glu Tyr Leu
            20

<210> SEQ ID NO 3
<211> LENGTH: 20
<212> TYPE: PRT
<213> ORGANISM: Artificial Sequence
<220> FEATURE:
<223> OTHER INFORMATION: Modified protein from Hirudo medicinalis
<220> FEATURE:
<221> NAME/KEY: MISC_FEATURE
<222> LOCATION: (1)..(1)
<223> OTHER INFORMATION: Residue is a D-isomer
<220> FEATURE:
<221> NAME/KEY: MISC_FEATURE
<222> LOCATION: (12)..(12)
<223> OTHER INFORMATION: Residue is a D-isomer

<400> SEQUENCE: 3

Phe Pro Arg Pro Gly Gly Gly Gly Asn Gly Asp Phe Glu Glu Ile Pro
1               5                   10                  15

Glu Glu Tyr Leu
            20
```

US 7,582,727 B1

PHARMACEUTICAL FORMULATIONS OF BIVALIRUDIN AND PROCESSES OF MAKING THE SAME

INCORPORATION BY REFERENCE

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

Various embodiments of the present invention are generally directed towards a method for preparing a pharmaceutical batch(es) or a pharmaceutical formulation(s) comprising bivalirudin as the active ingredient. Some embodiments of the present invention are also directed towards a pharmaceutical batch(es) or a pharmaceutical formulation(s) comprising bivalirudin as the active ingredient. For example, certain embodiments of the present invention relate to pharmaceutical batch(es) or pharmaceutical formulation(s) of a drug product having reduced levels of a major degradation product, i.e., $Asp^9$-bivalirudin, which may contribute to improved stability and shelf-life. In some embodiments, the pharmaceutical batch(es) or pharmaceutical formulation(s) is characterized by a maximum impurity level of $Asp^9$-bivalirudin that does not exceed about 0.6%. In various embodiments, the pharmaceutical batch(es) or pharmaceutical formulation(s) of the present invention are characterized by a reconstitution time that does not exceed about 42 seconds. Various embodiments of the invention further generally relate to an injectable dosage form comprising a pharmaceutical formulation and a vehicle, and methods of administering the injectable dosage form.

BACKGROUND OF THE INVENTION

Anticoagulants are substances that prevent blood from clotting. They are commonly used during percutaneous coronary intervention (PCI) and other catherization techniques in order to reduce bleeding complications. One class of anticoagulants is direct thrombin inhibitors that disrupt the activity of thrombin, an important protein in the coagulation cascade. In particular, bivalirudin (ANGIOMAX®), which directly inhibits thrombin by specifically binding to both its catalytic site and to the anion-binding exosite, is regarded as a highly effective anticoagulant for use during catherization procedures.

Bivalirudin, also known as Hirulog-8, is a synthetic congener of the naturally occurring thrombin peptide inhibitor hirudin, which is found in the saliva of the medicinal leech *Hirudo medicinalis*. Hirudin consists of 65 amino acids, although shorter peptide segments have proven to be effective as thrombin inhibitors. U.S. Pat. No. 5,196,404 (incorporated herein by reference) discloses bivalirudin among these shorter peptides that demonstrate an anticoagulant activity. However, in contrast to hirudin, bivalirudin is a reversible inhibitor, which is ideal for temporary prevention of blood clotting during catherization procedures.

In light of the medical and therapeutic applications of bivalirudin, it is essential that the bivalirudin formulation maintains a high level of purity. The bivalirudin formulation is a compounded formulation containing bivalirudin, e.g., bivalirudin undergoes a compounding process following its synthesis so that it is usable and stable for medical and therapeutic applications.

Impurities such as $Asp^9$-bivalirudin (deamidation of asparagine at position 9 of bivalirudin to aspartic acid) and D-$Phe^{12}$-bivalirudin (isomerization of L-phenylalanine at position 12 of bivalirudin to the D-isomer) may be generated during the synthesis of bivalirudin. Consequently, processes for synthesizing bivalirudin have been developed to minimize the generation of impurities. However, impurities can also be produced during the compounding process, i.e., the process to generate a formulation of bivalirudin. It has been shown that various compounding processes can result in formulations that have up to 12% of $Asp^9$-bivalirudin, which may affect product stability and shelf-life. Therefore, development of a compounding process for formulating bivalirudin that consistently generates formulations having low levels of impurities is desirable.

Citation or identification of any document in this application is not an admission that such document is available as prior art to the present invention.

SUMMARY OF THE INVENTION

Various embodiments of the present invention relates to a compounding process for preparing a pharmaceutical batch(es) of a drug product or a pharmaceutical formulation(s) comprising bivalirudin as an active ingredient. In certain embodiments, the compounding process comprises (i) dissolving bivalirudin in a solvent to form a first solution; (ii) efficiently mixing a pH-adjusting solution with the first solution to form a second solution, wherein $Asp^9$-bivalirudin in the second solution is minimized; and (iii) removing the solvent from the second solution.

In some embodiments, the pH of the second solution does not exceed about 8. In some embodiments, the pH of the second solution does not exceed about 7. In further embodiments, the pH of the second solution does not exceed about 6.

In certain embodiments, efficient mixing is achieved by adding the pH-adjusting solution to the first solution, by adding the first solution to the pH-adjusting solution, or a combination thereof. In some embodiments, the pH-adjusting solution is added to the first solution in portions. In further embodiments, the pH-adjusting solution is added to the first solution at a constant rate.

In some embodiments, efficient mixing is achieved by using one or more mixing devices. In certain embodiments, the mixing device is selected from a group consisting of a paddle mixer, magnetic stirrer, shaker, re-circulating pump, homogenizer, and any combination thereof. In some embodiments, the mixing device is a homogenizer, a paddle mixer, or a combination thereof.

In further embodiments, the efficient mixing is achieved through high shear mixing.

In certain embodiments, removal of the solvent from the second solution is achieved through lyophilization.

In some embodiments, the compounding process may further comprise sterilization of the second solution before removal of the solvent. In certain embodiments, sterilization is achieved by aseptic filtration.

Various embodiments of the present invention also relate to a pharmaceutical batch(es) or a pharmaceutical formulation(s) prepared by the compounding process of the invention. In certain embodiments, a pharmaceutical batch(es) or pharmaceutical formulation(s) is characterized by a maximum impurity level of Asp$^9$-bivalirudin that does not exceed about 0.6%. In some embodiments, a pharmaceutical batch(es) or pharmaceutical formulation(s) is characterized by a maximum total impurity level that does not exceed about 2%. In additional embodiments, a pharmaceutical batch(es) or pharmaceutical formulation(s) is characterized by a maximum reconstitution time that does not exceed about 42 seconds.

In addition, various embodiments of the present invention relate to a pharmaceutical batch(es) of a drug product or a pharmaceutical formulation(s) comprising bivalirudin as an active ingredient for use as an anticoagulant in a subject in need thereof, said pharmaceutical batch(es) or pharmaceutical formulation(s) prepared by a compounding process comprising: (i) dissolving bivalirudin in a solvent to form a first solution; (ii) efficiently mixing a pH-adjusting solution with the first solution to form a second solution; and (iii) removing the solvent from the second solution.

In certain embodiments, the pharmaceutical batch(es) or pharmaceutical formulation(s) is characterized by a maximum impurity level of Asp$^9$-bivalirudin that does not exceed about 0.6%. In some embodiments, the maximum impurity level of Asp$^9$-bivalirudin does not exceed about 0.4%. In further embodiments, the maximum impurity level of Asp$^9$-bivalirudin does not exceed about 0.3%.

In some embodiments of the present invention, the pharmaceutical batch(es) or pharmaceutical formulation(s) is characterized by a maximum total impurity level that does not exceed about 2%. In certain embodiments, the maximum total impurity level does not exceed about 1%. In additional embodiments, the pharmaceutical batch(es) or pharmaceutical formulation(s) is characterized by a maximum level of D-Phe$^{12}$-bivalirudin that does not exceed about 2.5%.

In other embodiments, the pharmaceutical batch(es) or pharmaceutical formulation(s) is characterized by a maximum reconstitution time that does not exceed about 42 seconds. In some embodiments, the maximum reconstitution time does not exceed about 30 seconds. In further embodiments, the maximum reconstitution time does not exceed about 21 seconds.

In some embodiments of the present invention, the pharmaceutically acceptable carrier comprises one or more of a bulking agent or a stabilizing agent. In certain embodiments, the pharmaceutically acceptable carrier is a bulking agent. In additional embodiments, the bulking agent is a sugar. In further embodiments, the sugar is mannitol.

In certain embodiments, efficient mixing is achieved by adding the pH-adjusting solution to the first solution, by adding the first solution to the pH-adjusting solution, or a combination thereof. In some embodiments, the pH-adjusting solution is added to the first solution at a constant rate. In further embodiments, efficient mixing is achieved by using one or more mixing devices. In yet additional embodiments, the efficient mixing is achieved through high shear mixing.

Moreover, various embodiments of the present invention relate to a pharmaceutical batch(es) of a drug product or pharmaceutical formulation(s) comprising bivalirudin as an active ingredient for use as an anticoagulant in a subject in need thereof, said pharmaceutical batch(es) or pharmaceutical formulation(s) prepared by a compounding process comprising: (i) dissolving bivalirudin in a solvent to form a first solution; (ii) efficiently mixing a pH-adjusting solution with the first solution to form a second solution; and (iii) removing the solvent from the second solution; wherein the pharmaceutical batch(es) or pharmaceutical formulation(s) are characterized by a maximum impurity level of Asp$^9$-bivalirudin that does not exceed about 0.6%.

Certain embodiments of the present invention also relate to a pharmaceutical batch(es) of a drug product or pharmaceutical formulation(s) comprising bivalirudin as an active ingredient for use as an anticoagulant in a subject in need thereof, said pharmaceutical batch(es) or pharmaceutical formulation(s) prepared by a compounding process comprising: (i) dissolving bivalirudin in a solvent to form a first solution; (ii) efficiently mixing a pH-adjusting solution with the first solution to form a second solution; and (iii) removing the solvent from the second solution; wherein the pharmaceutical batch(es) or pharmaceutical formulation(s) is characterized by a maximum reconstitution time that does not exceed about 42 seconds.

Furthermore, various embodiments of the present invention relate to a pharmaceutical batch(es) of a drug product or a pharmaceutical formulation(s) comprising bivalirudin as an active ingredient for use as an anticoagulant in a subject in need thereof. Some embodiments of the present invention also relate to a pharmaceutical batch(es) of a drug product or a pharmaceutical formulation(s) comprising bivalirudin as an active ingredient for use as an anticoagulant in a subject in need thereof, wherein the pharmaceutical batch(es) or pharmaceutical formulation(s) is characterized by a maximum impurity level of Asp$^9$-bivalirudin that does not exceed about 0.6%.

In some embodiments, the maximum impurity level of Asp$^9$-bivalirudin does not exceed about 0.4%. In certain embodiments, the maximum impurity level of Asp$^9$-bivalirudin does not exceed about 0.3%.

In additional embodiments, the pharmaceutical batch(es) or pharmaceutical formulation(s) is further characterized by a maximum total impurity level that does not exceed about 2%. In certain embodiments, the maximum total impurity level does not exceed about 1%. In some embodiments, the maximum total impurity level does not exceed about 0.5%.

In certain embodiments of the invention, the pharmaceutical batch(es) or pharmaceutical formulation(s) is further characterized by a maximum level of D-Phe$^{12}$-bivalirudin that does not exceed about 2.5%.

In some embodiments, the pharmaceutically acceptable carrier comprises one or more of a bulking agent or a stabilizing agent. In certain embodiments, the pharmaceutically acceptable carrier is a bulking agent. In further embodiments, the bulking agent is a sugar. In yet additional embodiments, the sugar is mannitol.

Some embodiments of the present invention relate to a pharmaceutical batch(es) of a drug product or pharmaceutical formulation(s) comprising bivalirudin as an active ingredient for use as an anticoagulant in a subject in need thereof, wherein the pharmaceutical batch(es) or pharmaceutical formulation(s) is characterized by a maximum reconstitution time that does not exceed about 42 seconds.

In certain embodiments, the maximum reconstitution time does not exceed about 30 seconds. In some embodiments, the maximum reconstitution time does not exceed about 21 seconds.

In some embodiments of the invention, the pharmaceutically acceptable carrier comprises one or more of a bulking agent or a stabilizing agent. In certain embodiments, the pharmaceutically acceptable carrier is a bulking agent. In further embodiments, the bulking agent is a sugar. In yet additional embodiments, the sugar is mannitol.

Also, various embodiments of the present invention relate to a pharmaceutical batch(es) of a drug product or pharmaceutical formulation(s) comprising bivalirudin as an active ingredient for use as an anticoagulant in a subject in need thereof, wherein the pharmaceutical batch(es) or pharmaceutical formulation(s) is characterized by a maximum impurity level of Asp$^9$-bivalirudin that does not exceed about 0.6%, a maximum total impurity level that does not exceed about 2%, and a maximum reconstitution time that does not exceed about 42 seconds.

These and other embodiments are disclosed or are obvious from and encompassed by, the following Detailed Description.

DETAILED DESCRIPTION

Various embodiments of the present invention relate to a compounding process for preparing a pharmaceutical batch(es) of a drug product, which results in pharmaceutical formulations comprising bivalirudin and a pharmaceutically acceptable carrier. Certain embodiments of the present invention also relate to a pharmaceutical batch(es) of a drug product, resultant pharmaceutical formulation(s) comprising bivalirudin and a pharmaceutically acceptable carrier, and an injectable dosage form comprising the pharmaceutical formulation and a vehicle.

As used here, "batch" or "pharmaceutical batch" refers to material produced by a single execution of a compounding process of various embodiments of the present invention. "Batches" or "pharmaceutical batches" as defined herein may include a single batch, wherein the single batch is representative of all commercial batches (see generally, Manual of Policies and Procedures, Center for Drug Evaluation and Research, MAPP 5225.1, Guidance on the Packaging of Test Batches at 1), and wherein the levels of, for example, Asp$^9$-bivalirudin, total impurities, and largest unknown impurity, and the reconstitution time represent levels for all potential batches made by said process. "Batches" may also include all batches prepared by a same compounding process.

The term "drug product" herein refers to an active ingredient and a pharmaceutically acceptable carrier.

The term "formulation" or "pharmaceutical formulation" refers to a unit dose of an active pharmaceutical ingredient and a pharmaceutically acceptable carrier, which is prepared by the various processes in certain embodiments of the present invention. In the case of the present pharmaceutical formulation, the active pharmaceutical ingredient is bivalirudin.

The term "carrier" refers to any component of the pharmaceutical batch(es) or pharmaceutical formulation(s) that, for example, serves as a bulking agent or functions as a stabilizing agent for the active ingredient. A bulking agent refers to any material that fills or provides volume to the active ingredient. Examples of appropriate bulking agents may include, but are not limited to, sugars such as mannitol, sucrose, lactose, fructose and trehalose.

A stabilizing agent refers to any material which serves to minimize degradation of the active ingredient. Examples of stabilizing agents may include, but are not limited to, antioxidants, buffering agents, preservatives, etc.

Bivalirudin has the chemical name of D-Phenylalanyl-L-Prolyl-L-Arginyl-L-Prolyl-Glycyl-Glycyl-Glycyl-Glycyl-L-Asparagyl-Glycyl-L-Aspartyl-L-Phenylalanyl-L-Glutamyl-L-Glutamyl-L-Isoleucyl-L-Prolyl-L-Glutamyl-L-Glutamyl-L-Tyrosyl-L-Leucine trifluoroacetate (salt) hydrate and has a molecular weight of 2180 daltons. Bivalirudin is made up of the amino acid sequence: (D-Phe)-Pro-Arg-Pro-Gly-Gly-Gly-Gly-Asn-Gly-Asp-Phe-Glu-Glu-Ile-Pro-Glu-Glu-Tyr-Leu (SEQ ID NO: 1). Methods for the synthesis of bivalirudin may include, but are not limited to, solid-phase peptide synthesis, solution-phase peptide synthesis, or a combination of solid-phase and solution-phase procedures (e.g., U.S. Pat. No. 5,196,404; Okayama et al., *Chem. Pharm. Bull.* 1996, 44: 1344-1350; Steinmetzer et al., *Eur. J. Biochem.* 1999, 265: 598-605; PCT Patent Application WO 91/02750).

As described above, Asp$^9$-bivalirudin is formed due to deamidation of asparagine at position 9 of bivalirudin to aspartic acid. The amino acid sequence of Asp$^9$-bivalirudin is: (D-Phe)-Pro-Arg-Pro-Gly-Gly-Gly-Gly-Asp-Gly-Asp-Phe-Glu-Glu-Ile-Pro-Glu-Glu-Tyr-Leu (SEQ ID NO: 2). Further, D-Phe$^{12}$-bivalirudin is generated from isomerization of L-phenylalanine at position 12 of bivalirudin to the D-isomer. The amino acid sequence of D-Phe$^{12}$-bivalirudin is (D-Phe)-Pro-Arg-Pro-Gly-Gly-Gly-Gly-Asn-Gly-Asp-(D-Phe)-Glu-Glu-Ile-Pro-Glu-Glu-Tyr-Leu (SEQ ID NO: 3)

Bivalirudin inhibits blood clotting by binding to thrombin, a key serine protease in blood clot formation. This synthetic 20 amino acid peptide binds to thrombin at the catalytic site and at the anion-binding exocite, thereby inhibiting thrombin. Thrombin plays a central role in hemostasis. The coagulation pathway initiates clotting when thrombin, a serine protease, converts fibrinogen into fibrin. Additionally, thrombin activates Factor XIII into Factor XIIIa (the latter which links fibrin polymers covalently), Factors V and VIII (which promote thrombin generation), and platelets (which help propagate the thrombus).

The method of delivery of bivalirudin may be through intravenous administration. Bivalirudin may be supplied in single-use vials as a white lyophilized sterile cake. Each single-use vial may contain about 250 mg of bivalirudin. When reconstituted with a sterile aqueous solution for injection, the product yields a clear to opalescent, colorless to slightly yellow, solution. Such a solution has a pH of about 5-6.

The pharmaceutical batch(es) or pharmaceutical formulation(s) according to certain embodiments of the present invention may be used in any application which requires altered or inhibited thrombin activity. The pharmaceutical batch(es) or pharmaceutical formulation(s) may be used to alter or inhibit the coagulation cascade, for example, as an anticoagulant.

Approved indications include treatment in patients with unstable angina undergoing percutaneous transluminal coronary angioplasty; administration with the provisional use of glycoprotein IIb/IIIa inhibitor for use as an anticoagulant in patients undergoing percutaneous coronary intervention (PCI); and treatment in patients with, or at risk of, heparin-induced thrombocytopenia (HIT) or heparin-induced thrombocytopenia and thrombosis syndrome (HITTS) undergoing PCI. Also, the pharmaceutical batch(es) or pharmaceutical formulation(s) according to various embodiments of the present invention can be used for the prevention and treatment of venous thromboembolic disease.

Process for Preparing a Pharmaceutical Batch(es) or a Pharmaceutical Formulation(s)

Various embodiments of the present invention relate to a compounding process for preparing a pharmaceutical batch(es) or pharmaceutical formulation(s) comprising bivalirudin.

1) Dissolving Bivalirudin in a Solvent to Form a Bivalirudin Solution

In the compounding process of various embodiments of the present invention, bivalirudin may be dissolved in a solvent to form a bivalirudin solution. Bivalirudin may be commercially purchased or synthesized by various procedures as described above. The concentration of bivalirudin in the solvent may be between about 0.010 g/mL and about 1 g/mL, or between about 0.050 g/mL and about 0.1 g/mL. Solvents may include aqueous and non-aqueous liquids, including but not limited to, mono- and di-alcohols such as methanol, ethanol, isopropyl alcohol, and propylene glycol; polyhydric alcohols such as glycerol and polyethylene glycol; buffers; and water.

The solvent may comprise carriers such as sugars. For example, the sugar may be a monosaccharide such as glucose or fructose; a disaccharide such as sucrose, maltose, or trehalose; an oligosaccharide; or a polysaccharide. Alternatively, the sugar may be a sugar alcohol, such as sorbitol or mannitol. The quantity of carrier in the solvent may be adjusted to provide a pharmaceutical batch or pharmaceutical formulation preferably having a ratio of the carrier to the active ingredient of between about 5:1 and about 1:10, or between about 1:1 and about 1:4, or more preferably about 1:2.

Bivalirudin can be dissolved in the solvent by methods known in the art, preferably by adding the bivalirudin to the solvent. For example, bivalirudin may be added to the solvent rapidly, slowly, in portions, at a constant rate, at a variable rate, or a combination thereof. A mixing device known in the art may be used to dissolve bivalirudin. Examples of mixing devices may include, but are not limited to, a paddle mixer, magnetic stirrer, shaker, re-circulating pump, homogenizer, and any combination thereof. The mixing device may be applied at a mixing rate between about 100 and about 2000 rpm, or between about 300 and about 1500 rpm. The solution resulting from dissolving the bivalirudin in the solvent is referred to here as the "bivalirudin solution" or alternatively the "first solution."

2) Mixing a pH-Adjusting Solution with the Bivalirudin Solution to Form a Compounding Solution The compounding process may comprise mixing a pH-adjusting solution with the bivalirudin solution to form a compounding solution. The pH-adjusting solution may be prepared before, after, or simultaneously with, the bivalirudin solution.

The pH-adjusting solution may comprise a base dissolved in a solvent, wherein the solvent is referred to here as the "pH-adjusting solution solvent." In other words, the solution resulting from the combination of the base with the pH-adjusting solution solvent is referred to here as the "pH-adjusting solution." The pH-adjusting solution may also comprise a neat base such as pyridine or a volatilizable base such as ammonium carbonate.

The base may be an organic base or an inorganic base. The terms "inorganic base" and "organic base," as used herein, refer to compounds that react with an acid to form a salt; compounds that produce hydroxide ions in an aqueous solution (Arrhenius bases); molecules or ions that capture hydrogen ions (Bronsted-Lowry bases); and/or molecules or ions that donate an electron pair to form a chemical bond (Lewis bases). In certain processes, the inorganic or organic base may be an alkaline carbonate, an alkaline bicarbonate, an alkaline earth metal carbonate, an alkaline hydroxide, an alkaline earth metal hydroxide, an amine, or a phosphine. For example, the inorganic or organic base may be an alkaline hydroxide such as lithium hydroxide, potassium hydroxide, cesium hydroxide, or sodium hydroxide; an alkaline carbonate such as calcium carbonate or sodium carbonate; or an alkaline bicarbonate such as sodium bicarbonate.

Solvents may include aqueous and non-aqueous liquids, including but not limited to, mono- and di-alcohols such as methanol, ethanol, isopropyl alcohol, and propylene glycol; polyhydric alcohols such as glycerol and polyethylene glycol; buffers; and water. The pH-adjusting solution solvent may comprise carriers such as dissolved sugars. For instance, the sugar may be a monosaccharide such as glucose or fructose; a disaccharide such as sucrose, maltose, or trehalose; an oligosaccharide; or a polysaccharide. The sugar may also be a sugar alcohol, such as sorbitol or mannitol. The quantity of the carrier in the pH-adjusting solution solvent may be adjusted to provide the final product as described above.

The base is mixed or dissolved in the pH-adjusting solution solvent. The mixing or dissolution can be performed by methods known in the art. For instance, the base may be added to the pH-adjusting solution solvent rapidly, slowly, in portions, at a constant rate, at a variable rate, or a combination thereof. Also, a mixing device known in the art may be used to mix the base and the pH-adjusting solution solvent. Examples of mixing devices may include, but are not limited to, a paddle mixer, magnetic stirrer, shaker, re-circulating pump, homogenizer, and any combination thereof. The mixing device may be applied at a mixing rate between about 100 and about 1500 rpm, or between about 300 and about 1200 rpm. The base is added/mixed with the pH-adjusting solution solvent in a quantity that will result in a pH-adjusting solution that is characterized as being between about 0.01 N and about 5 N, or between about 0.1 N and 1 N.

The pH-adjusting solution may then be mixed with the bivalirudin solution. This mixing may occur by adding the pH-adjusting solution to the bivalirudin solution. Alternatively, the bivalirudin solution may be added to the pH-adjusting solution, or the pH-adjusting solution and the bivalirudin solution may be added simultaneously (into a separate vessel), or there may be a combination of these addition methods thereof. It is important during the adding or mixing of the pH-adjusting solution and the bivalirudin solution that pH is controlled. See below. The solution resulting from mixing the pH-adjusting solution and the bivalirudin solution is referred to here as the "compounding solution," or the "second solution." The compounding solution or the second solution can refer to the bivalirudin solution during or after the pH-adjusting solution is added, or can refer to the pH-adjusting solution during or after the bivalirudin solution is added, or can refer to the resulting solution formed during or after both the pH-adjusting solution and the bivalirudin solution are added together.

The mixing of the pH-adjusting solution and the bivalirudin solution may occur under controlled conditions. For example, temperature may be controlled by means known in the art, such as by mixing the pH-adjusting solution and the bivalirudin solution in a vessel inside a cooling jacket. The temperature may be set between about 1° C. and about 25° C., or between about 2° C. and about 10° C. In some instances, the temperature may exceed 25° C. for limited periods of time. Also, the mixing of the pH-adjusting solution and the bivalirudin solution may occur under controlled conditions such as under nitrogen, etc.

The pH-adjusting solution will be efficiently mixed with the bivalirudin solution to form the compounding solution. Efficient mixing of the pH-adjusting solution with the bivalirudin solution will minimize levels of $Asp^9$-bivalirudin in the compounding solution. "Minimize" as used herein refers to the generation of a level of $Asp^9$-bivalirudin in the compounding solution that is less than about 0.6%, or less than about 0.4%, or less than about 0.3%.

Critical to the efficient mixing is the fact that the isoelectric point of bivalirudin is about 3.6. As the bivalirudin solution itself has a pH of between about 2.5 and about 2.8, and the compounding solution is adjusted to a final pH of between about 5.1 and about 5.5, a portion of bivalirudin precipitates out during the addition of the pH-adjusting solution. The characteristics of this precipitate are critical to regulating and controlling $Asp^9$-bivalirudin levels.

For example, if the pH-adjusting solution is introduced without efficient mixing, a dense precipitate may form. This dense precipitate may result in a slower dissolution and the surrounding solution being maintained at a high pH for extended time. Although the concentration of bivalirudin in the solution phase is low, it is also very susceptible to $Asp^9$-bivalirudin generation at this high pH.

Conversely, if the pH-adjusting solution is efficiently mixed with the bivalirudin solution, the formed precipitate is amorphous. The amorphous character allows for a more rapid re-dissolution of the precipitate and a better control of pH throughout the compounding process. Thus, process operations to control the pH transition through efficient mixing provide a significant process improvement and control of $Asp^9$-bivalirudin levels.

Not wishing to be bound by theory, $Asp^9$-bivliarudin may also be generated by high pH or "hot spots," which are defined here as concentrated sites in the compounding solution that have much higher pH levels than the surrounding environment. An example of a hot spot is a site in the compounding solution having a pH of about 12, while the surrounding solution has a pH of about 5. $Asp^9$-bivliarudin may also be generated by high pH levels in the compounding solution in general. It has been found that efficient mixing reduces the generation of "hot spots" or high levels of pH in the compounding solution while the pH-adjusting solution and the bivalirudin solution are being added/mixed. Thus, efficient mixing may control the overall pH level of the compounding solution to a level not exceeding about 8, or a level not exceeding about 7, or a level not exceeding about 6, or even a level not exceeding about 5.5.

Efficient mixing is characterized by minimizing levels of $Asp^9$-bivalirudin in the compounding solution. This may be achieved through various methods. One such method may be to add or combine the pH-adjusting solution and bivalirudin solution portion-wise, i.e., in portions. For instance, the pH-adjusting solution may be added to the bivalirudin solution in portions of set quantities, wherein each addition is separated by a period of time. The quantity of pH-adjusting solution may be approximately equal or may vary among the portions. For example, the pH-adjusting solution may be added in four portions, wherein each portion comprises about 25% of the total pH-adjusting solution volume. As another example, the pH-adjusting solution may be added in three portions, such that the first portion comprises about 45% of the total pH-adjusting solution volume, the second portion comprises about 30% of the total pH-adjusting solution volume, and the third portion comprises about 25% of the total pH-adjusting solution volume.

The pH-adjusting solution may also be added in portions such that there is a combination of equal and unequal quantities. For instance, the pH-adjusting solution may be divided into four portions, wherein the first portion comprises about 45% of the total pH-adjusting solution volume, the second portion comprises about 25% of the total pH-adjusting solution volume, and the third and fourth portions each comprise about 15% of the total pH-adjusting solution volume.

The period of time between the addition of each portion may vary. This period may be a set duration of time regardless of the number of portions and/or volume of the portions to be added. Alternatively, the period of time may vary according to the number of portions and/or volume of the portions to be added. For example, the period of time between adding four equal portions may be about 5 minutes between each addition. As another example, the period of time after adding a first portion comprising about 60% of the total pH-adjusting solution volume may be about 15 minutes, while the period of time after adding a second portion comprising about 40% of the total pH-adjusting solution volume may be about 5 minutes.

The period of time between the addition of each portion may also be based upon a set total time for adding the pH-adjusting solution. For instance, if the total time for adding a pH-adjusting solution is set at about 20 minutes, then the period of time after adding each portion comprising about 25% of the total pH-adjusting solution volume may be about 5 minutes. In certain embodiments of the present invention, the total time for adding the pH-adjusting solution may be a duration of between about 5 minutes and about 40 minutes, or between about 10 minutes and about 30 minutes, or between about 15 minutes and about 25 minutes.

Efficient mixing may also be achieved by adding the pH-adjusting solution to the bivalirudin solution at a constant rate. The pH-adjusting solution may be added at a rate of between about 0.5% and about 50% of the total pH-adjusting solution volume, per minute; or between about 1% and about 25% of the total pH-adjusting solution volume, per minute; or between about 3% and about 8% of the total pH-adjusting solution volume, per minute.

The pH-adjusting solution may alternatively be added at a variable rate to the bivalirudin solution. As an example, the rate may increase from about 5% to about 20% of the total pH-adjusting solution volume per minute during the addition of the pH-adjusting solution.

The pH-adjusting solution may also be added to the bivalirudin solution portion-wise, wherein each portion is added at a constant or variable rate. The portions may be added in equal amounts, unequal amounts, or a combination thereof. Further, each portion may be added at the same or different constant rates, or the same or different variable rates, or a combination thereof. As an example, the first portion comprising 60% of the total pH-adjusting solution may be added at 5% of the portion volume per minute, while four subsequent portions each comprising about 10% of the total pH-adjusting solution may be added at 10% of the portion volume per minute.

Furthermore, efficient mixing may be achieved through the use of one or more mixing devices. Examples of mixing devices that may be used in various embodiments of the present invention may include, but are not limited to, a paddle mixer, magnetic stirrer, shaker, re-circulating pump, homogenizer, and any combination thereof. The mixing rate of, for instance, a paddle mixer may be between about 100 rpm and 1000 rpm, or between about 400 rpm and about 800 rpm. The mixing rate for, as an example, a homogenizer (i.e., high shear mixing) may be between about 300 and about 6000 rpm, or between about 1500 rpm and about 3000 rpm.

Since most proteins and peptides are susceptible to degradation by high shear, it was initially thought that bivalirudin could only be formulated using a compounding process employing low shear. Surprisingly, high shear mixing, such as through the use of a homogenizer, could successfully be used in the compounding process.

The mixing device may mix continuously during the addition of the pH-adjusting solution, or at specific periods of time, e.g., between the additions of portions, after the pH-adjusting solution is added, etc.

In addition, more than one mixing device may be used when the pH-adjusting solution is added to the bivalirudin solution. For example, a paddle mixer may be used at the surface of the bivalirudin solution and a homogenizer may be used near the bottom of the bivalirudin solution. When more than one mixing device is used, they may be operated at the same mixing rate or different mixing rates, or a combination thereof. The mixing devices may also be operated at the same periods of time, at different periods of time, or a combination thereof, during the addition of the pH-adjusting solution. Similarly, a mixing device may be used with the addition of the bivalirudin solution to the pH-adjusting solution, or with the addition of the pH-adjusting solution and the bivalirudin solution together.

Moreover, efficient mixing may be achieved through adding the pH-adjusting solution to specific sites within the bivalirudin solution. For instance, the pH-adjusting solution may be added to the surface of the bivalirudin solution or to the bottom of the bivalirudin solution. In the cases wherein a mixing device is used, the pH-adjusting solution may be added to the site of the mixing device, e.g., at the site of the paddles of the paddle mixer or the blades of the homogenizer. The pH-adjusting solution may also be added to more than one site in the bivalirudin solution; for example, the pH-adjusting solution may be added simultaneously at the top of the bivalirudin solution and at the site of the mixing device. Alternatively, the bivalirudin solution may be added to the pH-adjusting solution at specific sites and at more than one site within the pH-adjusting solution, as described above.

Optionally, once the compounding solution is formed, the pH or the final volume of the compounding solution may be adjusted to a specified level before removal of the solvent (see below). The pH or volume can be adjusted using methods known in the art, for instance, the addition of a pH-adjusting solution as described above.

The compounding solution may also be sterilized before the removal of solvent. The compounding solution may undergo aseptic filtration using, for example, a 0.2 µm disposable membrane filter, to sterilize the compounding solution. Techniques of sterilizing the compounding solution are known in the art (see, e.g., Berovic, *Biotechnol. Annu. Rev.* 2005, 11:257-79).

Furthermore, following sterilization, the compounding solution may be aliquoted into containers such as vials, bottles, ampoules, syringes, etc.

3) Removal of Solvent from the Compounding Solution

The compounding process of various embodiments of the invention may comprise removing solvents from the compounding solution in order to produce a pharmaceutical batch(es) or pharmaceutical formulation(s).

Removal of the solvent from the compounding solution may be achieved through lyophilization, which comprises freezing the compounding solution and then reducing the surrounding pressure to allow the frozen solvent/moisture in the material to sublime directly from a solid phase to a gas phase. The lyophilization process may be performed by methods known in the art (see, e.g., Liu, *Pharm. Dev. Technol.* 2006, 11: 3-28; Tang et al., *Pharm. Res.* 2004, 21: 191-200; Nail et al., *Pharm. Biotechnol.* 2002, 14: 281-360; U.S. Pat. Nos. 7,351,431, and 6,821,515, which are incorporated by reference).

For example, the compounding solution may be frozen using such techniques as, but not limited to, mechanical refrigeration, dry ice, and liquid nitrogen. The temperature may be cooled to a range of between about 0° C. and about −80° C., or between about −20° C. and about −55° C. The primary lyophilization step may be characterized by a lowered pressure of between about 0.05 torr and about 10 torr, or between about 1 torr and about 5 torr. The secondary lyophilization step may be characterized by a pressure between about 0.05 torr and about 5 torr, or between about 0.1 torr and about 3 torr. In other instances, only one lyophilization step may be required.

The solvent may also be removed from the compounding solution through other techniques such as spray drying and spray-freeze drying (see, e.g., Lee, *Pharm. Biotechnol.* 2002, 13: 135-58; Maa et al., *Curr. Pharm. Biotechnol.* 2000, 1:283-302), vacuum drying, super critical fluid processing, air drying, or other forms of evaporative drying, as known in the art.

Alternative Compounding Process

In other embodiments, an alternative compounding process for preparing a pharmaceutical batch(es) or a pharmaceutical formulation(s) comprising bivalirudin may comprise (1) preparing a bivalirudin solution, (2) mixing the bivalirudin solution with a pH-adjusting solution, (3) mixing the bivalirudin/pH-adjusting solution with a carrier to form a compounding solution.

The bivalirudin solution may be prepared by mixing bivalirudin in an aqueous or non-aqueous solvent as described above. The resulting bivalirudin solution may be mixed with a pH-adjusting solution as described above, including adding the bivalirudin solution to the pH-adjusting solution, or vice-versa.

The combined bivalirudin/pH-adjusting solution may then be mixed with a carrier such as a bulking agent or stabilizing agent as described above. For example, the carrier may be a sugar such as mannitol. The bivalirudin/pH-adjusting solution and the carrier may be efficiently mixed using methods described in this application.

Pharmaceutical Batch(es) or Pharmaceutical Formulation(s) Generated by the Compounding Process In the characterization of the pharmaceutical batch(es) and pharmaceutical formulation(s) generated by the compounding process, the levels of a parameter determined from the pharmaceutical formulation(s) prepared by a single execution of a compounding process are representative of the entire batch. Moreover, values for impurity levels include those amounts generated by the synthesis of the active pharmaceutical ingredient together with those levels generated by the compounding process.

Each pharmaceutical batch or pharmaceutical formulation prepared by the compounding process may be characterized by an impurity level of $Asp^9$-bivalirudin not exceeding about 1.5%, or not exceeding about 1%, or not exceeding about 0.6%, or not exceeding about 0.4%, or not exceeding about 0.3%.

The pharmaceutical batch(es) or the pharmaceutical formulation(s) prepared by the compounding process may be characterized by a total impurity level not exceeding about 6%, or not exceeding about 3%, or not exceeding about 2%, or not exceeding about 1%, or not exceeding about 0.5%. "Total impurity level" refers to the combined total of all measurable impurities in the pharmaceutical batch(es) or the pharmaceutical formulation(s).

The reconstitution time, i.e., time required to prepare the pharmaceutical batch(es) or the pharmaceutical formulation(s) for use, for the pharmaceutical batch(es) or the pharmaceutical formulation(s) may be characterized by a reconstitution time not exceeding about 180 seconds, or not exceeding about 72 seconds, or not exceeding about 42 seconds, or not exceeding about 30 seconds, or not exceeding about 21 seconds, or not exceeding about 15 seconds.

Reconstitution time may be determined, for example, by adding 5 mL of water to a unit dosage vial comprising the bivalirudin pharmaceutical formulation. Immediately after adding the appropriate diluent (e.g., water, saline, etc.), a timer is started. The vial is shaken vigorously, with inversion, for approximately 10 seconds. The vial is viewed to determine if the solid has dissolved. If the solid has not completely dissolved, the vial is shaken for another 10 seconds. These steps are repeated until all the solid dissolves, at which point the time is stopped and recorded.

The pharmaceutical batch(es) or the pharmaceutical formulation(s) prepared by the compounding process may relate to one or more of the characteristics described above.

Collectively, the compounding process of certain embodiments of the invention described herein may consistently generate pharmaceutical batches or pharmaceutical formulations having the same characteristics. As used herein, the use of the terms "consistent" or "consistently" in reference to the compounding process indicates that about 85% of the pharmaceutical batch(es) or pharmaceutical formulation(s) have a specific characteristic, or wherein about 90% of the pharmaceutical batch(es) or pharmaceutical formulation(s) have the characteristic, or about 95% of the pharmaceutical batch(es) or pharmaceutical formulation(s) have the characteristic, or about 99% of the pharmaceutical batch(es) or pharmaceutical formulation(s) have said characteristic, or 100% of the pharmaceutical batch(es) or pharmaceutical formulation(s) have said characteristic.

In various embodiments of the present invention, the pharmaceutical batch(es) or pharmaceutical formulation(s) generated by the compounding process may be characterized by consistently having a maximum impurity level of $Asp^9$-bivalirudin not exceeding about 1.5%, or not exceeding about 1%, or not exceeding about 0.6%, or not exceeding about 0.4%, or not exceeding about 0.3%.

The pharmaceutical batch(es) or pharmaceutical formulation(s) prepared by the compounding process may be characterized by consistently having a mean impurity level of $Asp^9$-bivalirudin not exceeding about 1.5%, or not exceeding about 0.5%, or not exceeding about 0.4%, or not exceeding about 0.3%.

The pharmaceutical batch(es) or pharmaceutical formulation(s) generated by the compounding process may be characterized by consistently having a maximum total impurity level not exceeding about 6%, or not exceeding about 3%, or not exceeding about 2%, or not exceeding about 1%, or not exceeding about 0.5%.

The pharmaceutical batch(es) or pharmaceutical formulation(s) generated by the compounding process may be characterized by consistently having a mean total impurity level not exceeding about 2%, or not exceeding about 1.3%, or not exceeding about 1.1%, or not exceeding about 0.5%.

The pharmaceutical batch(es) or pharmaceutical formulation(s) generated by the compounding process may be characterized by consistently having a maximum largest unknown impurity level not exceeding about 1%, or not exceeding about 0.5%, or not exceeding about 0.4%, or not exceeding about 0.3%.

The pharmaceutical batch(es) or pharmaceutical formulation(s) generated by the compounding process may be characterized by consistently having a mean largest unknown impurity level not exceeding about 1.0%, or not exceeding about 0.27%, or not exceeding about 0.25%, or not exceeding about 0.2%.

The pharmaceutical batch(es) or pharmaceutical formulation(s) generated by the compounding process may be characterized by consistently having a maximum reconstitution time not exceeding about 180 seconds, or not exceeding about 72 seconds, or not exceeding about 42 seconds, or not exceeding about 30 seconds, or not exceeding about 21 seconds.

The pharmaceutical batch(es) or pharmaceutical formulation(s) generated by the compounding process may be characterized by consistently having a mean reconstitution times not exceeding about 60 seconds, or not exceeding about 30 seconds, or not exceeding about 21 seconds, or not exceeding about 15 seconds.

Moreover, the pharmaceutical batch(es) or pharmaceutical formulation(s) generated by the compounding process may relate to one or more of the characteristics described above.

Pharmaceutical Batch(es) and Pharmaceutical Formulation(s)

Certain embodiments of the present invention relate to a pharmaceutical batch(es) or pharmaceutical formulation(s) comprising bivalirudin and a pharmaceutically acceptable carrier. The carrier is any component of the pharmaceutical batch(es) or pharmaceutical formulation(s) that, for example, serves as a bulking agent or functions as a stabilizing agent for the active ingredient.

The solvent may comprise carriers such as sugars. For example, the sugar may be a monosaccharide such as glucose or fructose; a disaccharide such as sucrose, maltose, or trehalose; an oligosaccharide; or a polysaccharide. Alternatively, the sugar may be a sugar alcohol, such as sorbitol or mannitol.

A pharmaceutical batch(es) or pharmaceutical formulation(s) may be characterized by an impurity level of $Asp^9$-bivalirudin not exceeding about 1.5%, or not exceeding about 1%, or not exceeding about 0.6%, or not exceeding about 0.4%, or not exceeding about 0.3%.

A pharmaceutical batch(es) or pharmaceutical formulation(s) may be characterized by a total impurity level not exceeding about 6%, or not exceeding about 3%, or not exceeding about 2%, or not exceeding about 1%, or not exceeding about 0.5%.

A pharmaceutical batch(es) or pharmaceutical formulation(s) may also be characterized by a reconstitution time not exceeding about 180 seconds, or not exceeding about 72 seconds, or not exceeding about 42 seconds, or not exceeding about 30 seconds, or not exceeding about 21 seconds, or not exceeding about 15 seconds.

Further, a pharmaceutical batch(es) or pharmaceutical formulation(s) may relate to one or more of the characteristics described above.

A pharmaceutical batch(es) or pharmaceutical formulation(s) may be characterized by a maximum impurity level of $Asp^9$-bivalirudin not exceeding about 1.5%, or not exceeding about 1%, or not exceeding about 0.6%, or not exceeding about 0.4%, or not exceeding about 0.3%. The pharmaceutical batch(es) or pharmaceutical formulation(s) may also be characterized by a mean impurity level of $Asp^9$-bivalirudin not exceeding about 1.5%, or not exceeding about 0.5%, or not exceeding about 0.4%, or not exceeding about 0.3%.

Moreover, a pharmaceutical batch(es) or formulation(s) may be characterized by a maximum total impurity level not exceeding about 6%, or not exceeding about 3%, or not exceeding about 2%, or not exceeding about 1%, or not exceeding about 0.5%. In addition, the batch(es) may be characterized by a mean total impurity level not exceeding about 2%, or not exceeding about 1.3%, or not exceeding about 1.1%, or not exceeding about 0.5%.

The batch(es) may also be characterized by a maximum largest unknown impurity level not exceeding about 1%, or not exceeding about 0.5%, or not exceeding about 0.4%, or not exceeding about 0.3%. The batch(es) may further be characterized by a mean largest unknown impurity level not exceeding about 1%, or not exceeding about 0.27%, or not exceeding about 0.25%, or not exceeding about 0.2%.

Yet, the batch(es) may be characterized by a maximum reconstitution time not exceeding about 180 seconds, or not exceeding about 72 seconds, or not exceeding about 42 seconds, or not exceeding about 30 seconds, or not exceeding about 21 seconds. Also, the batch(es) may be characterized by a mean reconstitution time not exceeding about 60 seconds, or not exceeding about 30 seconds, or not exceeding about 21 seconds, or not exceeding about 15 seconds.

Moreover, the pharmaceutical batch(es) or pharmaceutical formulation(s) may relate to one or more of the characteristics described above.

The pharmaceutical batch(es) or pharmaceutical formulation(s) may be generated by the compounding processes described above. Thus, the batch(es) may be prepared by a compounding process comprising dissolving bivalirudin in a solvent to form a bivalirudin solution, efficiently mixing a pH-adjusting solution with the bivalirudin solution to form a compounding solution, and removing solvents from the compounding solution. This compounding process includes all of the embodiments as described above.

Administering the Pharmaceutical Formulation

Various embodiments of the present invention further relate to a method of administering the pharmaceutical formulation of certain embodiments of the present invention to a subject, which comprises preparing an injectable dosage form, and then delivering the injectable dosage form to the subject parenterally.

The injectable dosage form is prepared by reconstituting the pharmaceutical formulation in a pharmaceutically acceptable vehicle. Methods of reconstituting the pharmaceutical formulation are well known in the art. Pharmaceutically acceptable vehicles are also well known in the art and can include, but are not limited to, water and saline for injection.

As an example, the injectable dosage form may be prepared by adding water to the pharmaceutical formulation and dissolving the pharmaceutical formulation. This solution can then be further diluted in 5% dextrose in water or 0.9% sodium chloride for injection.

Methods of delivering the injectable dosage form parenterally are well known in the art. For example, the injectable dosage form may be delivered intravenously.

The dosage form may be an intravenous bolus dose of between about 0.25 mg/kg and about 1.50 mg/kg, or between about 0.50 mg/kg to about 1.00 mg/kg, or about 0.75 mg/kg. This may be followed by an infusion of between about 1.25 mg/kg/h and about 2.25 mg/kg/h, or about 1.75 mg/kg/h for the duration of the procedure or treatment protocol. Five minutes after the bolus dose is administered, an additional bolus of between about 0.1 mg/kg and about 1.0 mg/kg, or about 0.3 mg/kg, may be given if needed.

The dosage form of various embodiments of the present invention can be indicated for use as an anticoagulant. Also, the dosage form can be used for the prevention and treatment of venous thromboembolic disease. Approved indications include treatment in patients with unstable angina undergoing percutaneous transluminal coronary angioplasty; administration with the provisional use of glycoprotein IIb/IIIa inhibitor for use as an anticoagulant in patients undergoing percutaneous coronary intervention (PCI); and treatment in patients with, or at risk of, heparin-induced thrombocytopenia (HIT) or heparin-induced thrombocytopenia and thrombosis syndrome (HITTS) undergoing PCI. Also, the dosage form can be used for the prevention and treatment of venous thromboembolic disease.

The injectable dosage form may be administered with other drug products such as glycoprotein (GP) IIb/IIIa inhibitor ((see, e.g., Allie et al., *Vasc. Dis. Manage.* 2006, 3: 368-375). Alternatively, the injectable dosage form may be combined with blood thinners including, but not limited to, coumadin, warfarin, and preferably, aspirin.

The invention will now be further described by way of the following non-limiting examples, which further illustrate the invention, and are not intended, nor should they be interpreted to, limit the scope of the invention.

EXAMPLES

Example 1

Generation of High Levels of $Asp^9$-Bivalirudin

A study was performed in three parts to determine levels of $Asp^9$-bivalirudin generated in batches prepared by compounding processes having different methods of mixing the pH-adjusting solution with the bivalirudin solution to form a compounding solution. More specifically, the study examined the effects of adding the pH-adjusting solution to the bivalirudin solution in portions with inefficient mixing, the effects of having high levels of pH in the compounding solution, and the effects of high shear mixing of the compounding solution on $Asp^9$-bivalirudin levels.

In a first part of the study, the bivalirudin solution (~600 mL) comprised bivalirudin at a concentration of ~0.1 mg/mL in a 2.64% w/w mannitol solution. The pH-adjusting solution (233 mL) comprised 0.5 N sodium hydroxide in a 2.64% w/w mannitol solution. $Asp^9$-bivalirudin levels were measured throughout the experiment by high-performance liquid chromatography (HPLC). pH was also measured through the experiment. One measurement of $Asp^9$-bivalirudin was taken immediately after the bivalirudin solution was formed (baseline).

The pH-adjusting solution was added to the bivalirudin solution in four equal portions over the total duration of about 1 hour at a temperature of 5-8° C., each addition separated by about 15 minutes. The resulting compounding solution was mixed at between 600 rpm and 700 rpm throughout the addition of the first and second portions of the pH-adjusting solution, and the pH and $Asp^9$-bivalirudin levels were recorded (measurements #1 and #2). During the addition of the third portion, the mixer was turned off and the pH and $Asp^9$-bivalirudin levels were recorded (measurement #3A). The mixture was then subjected to high shear mixing at 4000 rpm for 30 seconds and the pH and $Asp^9$-bivalirudin levels were recorded (measurement #3B). During addition of the fourth portion, the mixer was turned off and the levels of pH and $Asp^9$-bivaluridin were recorded (measurement #4A). Mixing was then continued for, at least, two minutes at 5300 rpm and the pH was and $Asp^9$-bilvairudun levels were recorded (measurement #4B). The mixing rate was decreased to about 3600 rpm for 1 hour and the pH and $Asp^9$-bivalirudin levels were recorded (measurement #5). A portion of the material from measurement #4a was allowed to stand for 7 hours and the pH and $Asp^9$-bivalirudin levels were recorded (measurement #6). The pH and $Asp^9$-bivalirudin levels are shown in Table 1.

TABLE 1 pH and average $Asp^9$-bivalirudin levels after addition of pH-adjusting solution in four equal portions with inefficient mixing.

| Meas-urement | Sample | pH | % $Asp^9$-bivalirudin |
|---|---|---|---|
| Baseline | Sample taken after bivalirudin solution was formed | ~2.5 | ~0.42 |
| #1 | Sample taken from compounding solution after addition of first portion of pH-adjusting solution to bivalirudin solution | 3.0 | — |
| #2 | Sample taken from compounding solution after addition of second portion of pH-adjusting solution to bivalirudin solution | 4.2 | 0.43 |
| #3A | Sample taken from compounding solution after addition of third portion of pH-adjusting solution to bivalirudin solution with no mixing | ~6 to 8 | 0.45 |
| #3B | Same as #3A, but after mixing | 5.0 | 0.74 |
| #4A | Sample taken from compounding solution after addition of fourth portion of pH-adjusting solution to bivalirudin solution, and after compounding solution sat for 10 minutes with no mixing | ~8.5 to 9 | 0.60 |
| #4B | Same as #4A, but after mixing | 6.0 to 6.5 | 0.57 |
| #5 | Same as #4A, but after high speed mixing for 1 hour | 5.0 | 0.71 |
| #6 | Same as #4A, but 7 hours later with no mixing | ~8.5 to 9 | 2.05 |

These results suggest that inefficient mixing of the compounding solution generates $Asp^9$-bivalirudin. Notably, during the addition of the pH-adjusting solution, a precipitate formed which may contain bivalirudin. Since the level of $Asp^9$-bivalirudin is based on a % analysis by HPLC of the amount of bivalirudin in solution, the level of $Asp^9$-bivalirudin appears to increase and decrease during the compounding process.

In a second part of the study, four portions of the final compounding solution from the first part of the study were removed. The pH levels of these portions were adjusted to 8, 9, 10, and 12, respectively, using additional pH-adjusting solution and high shear mixing on a Silverson Laboratory Emulsifier (Model L4RT).

Samples of the portion of the compounding solution adjusted to pH 8 were taken immediately, and after about 80 minutes, 300 minutes, and 370 minutes. Samples of the portion of the compounding solution adjusted to pH 9 were taken immediately, after about 80 minutes, and 300 minutes. Further, samples of the portion of the compounding solution adjusted to pH 10 and 12 were taken immediately, after about 80 minutes and 170 minutes. The results of the analyses for levels of $Asp^9$-bivalirudin in these samples are shown in Table 2.

TABLE 2

$Asp^9$-bivalirudin levels of portions adjusted to various pH levels.

| Measurement | Sample | pH | % $Asp^9$-bivalirudin |
|---|---|---|---|
| Baseline | Sample measured after bivalirudin solution was formed | 5 | 0.71 |
| #1 | Sample measured after pH was adjusted | 8 | 0.71 |
| | Sample measured after ~80 minutes | | 0.77 |
| | Sample measured after ~300 minutes | | 1.11 |
| | Sample measured after ~370 minutes | | 1.26 |

TABLE 2-continued $Asp^9$-bivalirudin levels of portions adjusted to various pH levels.

| Measurement | Sample | pH | % $Asp^9$-bivalirudin |
|---|---|---|---|
| #2 | Sample measured after pH was adjusted | 9 | 0.84 |
| | Sample measured after ~80 minutes | | 1.07 |
| | Sample measured after ~300 minutes | | 1.84 |
| #3 | Sample measured after pH was adjusted | 10 | 1.24 |
| | Sample measured after ~80 minutes | | 2.08 |
| | Sample measured after ~170 minutes | | 2.59 |
| #4 | Sample measured after pH was adjusted | 12 | 4.71 |
| | Sample measured after ~80 minutes | | 8.20 |
| | Sample measured after ~170 minutes | | 10.95 |

These results appear to show a relationship between pH, time, and the generation of $Asp^9$-bivalirudin.

In a third part of the study, the final compounding solution from the first part of the study was placed into a recirculation vessel for use in a recirculation water bath (Precision Model 181) to be subjected to high shear mixing using a Silverson Laboratory Emulsifier (Model L4RT). Prior to this study, it was thought that bivalirudin solutions were unstable to both heat and shear, thus requiring extreme care in handling bivalirudin during the compounding process. Before subjecting the compounding solution to high shear mixing, the level of $Asp^9$-bivalirudin was recorded (measurement #1). The compounding solution was then subjected to high shear mixing at ~6000 rpm for 30 minutes without use of the recirculation water bath; the temperature of the compounding solution due to the high shear mixing rose to about 36° C. A sample was then measured for $Asp^9$-bivalirudin level (measurement #2). The mixing speed was then slowed to 5000 rpm for 120 minutes and the temperature was measured at about 33° C., and another sample was analyzed for $Asp^9$-bivalirudin level (measurement #3). The $Asp^9$-bivalirudin levels are shown in Table 3.

TABLE 3

$Asp^9$-bivalirudin levels of the compounding solution undergoing different high shear mixing rates.

| Measurement | Sample | Temperature | % $Asp^9$-bivalirudin |
|---|---|---|---|
| #1 | Sample taken from the compounding solution before high shear mixing | RT~20° C. | 0.71 |
| #2 | Sample taken from the compounding solution after high shear mixing at 6000 rpm for 30 minutes | 36° C. | 0.71 |
| #3 | Sample as #2, but after mixing rate was reduced to 5000 rpm for 120 minutes | 33° C. | 0.75 |

These results also show that, unexpectedly, that bivalirudin is stable to high shear mixing conditions. Also, the temperature of the compounding solution did not, surprisingly, affect $Asp^9$-bivalirudin generation in this study.

Example 2

Effects of Adding the pH-Adjusting Solution in Two Portions to the Bivalirudin Solution on $Asp^9$-Bivalirudin Levels A study was performed to determine levels of $Asp^9$-bivalirudin generated in compounding solutions prepared by a compounding process involving the addition of the pH-adjusting solution to the bivalirudin solution in two portions.

The bivalirudin solution (~760 mL) comprised bivalirudin at a concentration of 0.050 mg/ml dissolved in a 2.64% w/w mannitol solution. The pH-adjusting solution (233 mL) comprised 0.5 N sodium hydroxide in a 2.64% w/w mannitol solution. The experiment was conducted at a temperature of about 8° C.

The pH-adjusting solution was divided into a 75% portion and a 25% portion of the total pH-adjusting solution volume. First, the pH and Asp$^9$-bivalirudin levels were measured before addition of the pH-adjusting solution (baseline). During addition of the 75% portion, at about 400 rpm, the pH was monitored during mixing until the pH achieved a constant level at which time the Asp$^9$-bivalirudin level was also measured (measurement #1). A portion of this material was allowed to sit for about 6.5 hours and the amount of Asp$^9$-bivaliridn was again measured (measurement #2). The 25% portion of the pH-adjusting solution was added about 30 minutes after the last base addition and mixing was continued at 400 rpm. The pH was initially recorded and then both the pH and Asp$^9$-bivalirudin levels were measured after about 30 minutes of mixing (measurement #3). The pH and Asp$^9$-bivalirudin levels were again recorded after mixing at 400 rpm overnight (measurement #4). The pH and Asp$^9$-bivalirudin levels are shown in Table 4.

Notably, after the 75% portion of the pH-adjusting solution was added, a large white mass precipitated from the compounding solution and formed a mass at the bottom of the vessel. The addition of the 25% portion did not induce any physical changes in the appearance of the mixture, and there was no additional precipitation. The white mass displayed little change after mixing for 30 minutes after the 25% portion was added, but dissolved after mixing overnight.

TABLE 4 pH and average Asp$^9$-bivalirudin levels after addition of pH-adjusting solution in two portions of 75% and 25% at 400 rpm.

| Measurement | Sample | pH | % Asp$^9$-bivalirudin |
|---|---|---|---|
| Baseline | Sample taken after bivalirudin solution was formed | 1.71 | 0.42 |
| #1 | Sample of the compounding solution taken after addition of 75% portion of the pH-adjusting solution to the bivalirudin solution | Peak at 12.2, then dropped to 8-9 | 0.44 |
| #2 | Same as #1, but after sitting for 6.5 hours with no stirring | — | 0.88 |
| #3 | Remaining 25% of pH-adjusting solution added | 12.4 initially, then dropped to 7.7 after 30 minutes | 1.85 (taken from the top) 2.19 (taken from the bottom) |
| #4 | Same as #3, but after mixing overnight | 5.0 | 1.57 |

These results indicate that addition of the pH-adjusting solution in two portions with inefficient mixing produces high levels of Asp$^9$-bivalirudin.

Example 3

Effect of Controlled Addition of pH Adjusting Solution at Different Mixing Rates on Asp$^9$-Bivalirudin Levels Asp$^9$-bivalirudin levels were assessed in compounding solutions prepared by a compounding process which comprised adding the pH-adjusting solution at a constant rate to the bivalirudin solution and mixing under high shear conditions.

The bivalirudin solution (675 mL) comprised 64.4 g dissolved in 2.64% w/w mannitol solution. The bivalirudin solution was divided in half for evaluation of adding the pH-adjusting solution at two different mixing rates. The bivalirudin solution was placed in a vessel with a high shear mixer.

The pH-adjusting solution (131.2 mL) comprised 0.5 N sodium hydroxide in a 2.64% w/w mannitol solution. The pH-adjusting solution was loaded into a burette, which was connected on the bottom to a tube with a hose. The tube was positioned at the base of the high shear mixer blade inside the mixing vessel containing the bivalirudin solution. A clamp was used to restrict the pH-adjusting solution from passing through the hose.

The speed of the high shear mixer (Silverson Laboratory Emulsifier Model L4RT) was set to either 1500 rpm or 3000 rpm. The clamp on the hose was removed and the pH-adjusting solution was then added to the bivalirudin solution at a controlled, constant rate of approximately 2 L/min.

For the solution mixed at 3000 rpm, addition of approximately 10 mL of the pH-adjusting solution resulted in a pH of the compounding solution of 5.25. The volume of the compounding solution was then adjusted to a final volume of 562.5 mL.

For the compounding solution mixed at 1500 rpm, after the pH-adjusting solution was added, the mixing speed was increased to approximately 4500 rpm for a short period of time to allow faster and complete dissolution, and then reduced to 1500 rpm until the solution was completely dissolved. After complete dissolution, the resulting compounding solution was moved from the vessel to a beaker which contained a stir bar. The solution was adjusted to a target pH of 5.3 using 19 mL of the pH-adjusting solution, and then the volume was adjusted to a final volume of 562.5 mL.

For both mixing conditions, the pH was monitored throughout the addition of the pH-adjusting solution to the bivalirudin solution to form the compounding solution. The level of Asp$^9$-bivalirudin was measured by HPLC before (baseline) addition of the pH-adjusting solution, after the addition of the pH-adjusting solution (measurement #2), and after the volume of the compounding solution was adjusted to mark (measurement #3). The results of the HPLC analysis are shown in Tables 5a and 5b.

Notably, when the compounding solution was mixed at 3000 rpm, a material precipitated as the pH-adjusting solution was added, first as a milky white dispersion, and then as a semi-transparent aggregate. By the time that all of the pH-adjusting solution was added, most of the precipitated material had dissolved.

Similarly, when the compounding solution was mixed at 1500 rpm, a material also precipitated as the pH-adjusting solution was added, first as a milky white dispersion, and then as a semi-transparent aggregate.

TABLE 5a pH and average $Asp^9$-bivalirudin levels before and after addition of pH-adjusting solution at 1500 rpm.

| Measurement | Sample | pH | % $Asp^9$-bivalirudin |
|---|---|---|---|
| Baseline | Sample taken before addition of pH-adjusting solution | ~2.5 | 0.38 |
| #1 | Sample taken of the compounding solution after addition of pH-adjusting solution | ~6.0 | 0.31 |
| #2 | Sample taken of the compounding solution after compounding solution was adjusted to mark | 5.3 | 0.34 |

TABLE 5b pH and average $Asp^9$-bivalirudin levels before and after addition of pH-adjusting solution at 3000 rpm.

| Measurement | Sample | pH | % $Asp^9$-bivalirudin |
|---|---|---|---|
| Baseline | Sample taken from bivalirudin solution before addition of pH-adjusting solution | ~2.5 | 0.43 |
| #1 | Sample taken of the compounding solution after addition of pH-adjusting solution | ~5.6 | 0.41 |
| #2 | Sample taken of the compounding solution after compounding solution was adjusted to mark | 5.25 | 0.40 |

These results indicate that there were no changes in $Asp^9$-bivalirudin levels before and after the addition of the pH-adjusting solution at a constant rate, and under high shear mixing conditions. Moreover, it was surprising that bivalirudin was not susceptible to degradation by high shear mixing even up to 4500 rpm, even though many peptides are susceptible to degradation by high shear mixing or by high temperatures.

Example 4

Effects of Rapidly Adding pH Adjusting Solution to the Bivalirudin Solution Under Inefficient Mixing Conditions—Large Scale Study The effects of rapidly adding the pH-adjusting solution to the bivalirudin solution under slow mixing conditions were studied. Multiple batches were generated by the same method.

The bivalirudin solution (~110 L) comprised bivalirudin at a concentration of 0.050 mg/ml dissolved in a 2.64% w/w mannitol solution. The pH-adjusting solution (~40 L) comprised 0.5 N sodium hydroxide in a 2.64% w/w mannitol solution.

The pH-adjusting solution was added to the bivalirudin solution either all at once, or rapidly in multiple portions, while the bivalirudin solution was mixed by two paddle mixers located at the top and bottom of the bivalirudin solution. Both paddle mixers operated at a rate of between about 400 and about 800 rpm. When the pH-adjusting solution was added to the bivalirudin solution, a large amount of a material precipitated. The precipitated material eventually dissolved after continued mixing. After the pH-adjusting solution was completely added and mixed, the compounding solution was sterile filtered and lyophilized, and the lyophilizate was analyzed by HPLC for impurity levels.

This study analyzed impurity levels and reconstitution times of the lyophilizate of 89 batches. Results from the study are displayed in Table 6 (note that not all of the samples were analyzed for each characteristic).

TABLE 6

Characteristics of the batches generated by the compounding process that features rapid addition of a pH-adjusting solution and inefficient mixing rates.

| | No. of batches | Mean ± SD | Maximum |
|---|---|---|---|
| $Asp^9$-bivalirudin (%) | 87 | 0.5 ± 0.4 | 3.6 |
| Total impurities (%) | 63 | 1.4 ± 0.5 | 3.0 |
| Largest unknown impurity (%) | 86 | 0.3 ± 0.1 | 0.5 |
| Reconstitution time (seconds) | 85 | 30 ± 12 | 72 |

According to these results, the batches displayed a maximum level of $Asp^9$-bivalirudin of 3.6%, while the mean level of $Asp^9$-bivalirudin was 0.5%. Furthermore, the standard deviations relative to the means were larger. These results suggest that the characteristics of the batches generated by this process may be variable.

Example 5

Effects of Adding pH Adjusting Solution at a Constant Rate and Under Efficient Mixing Conditions—Large Scale Study The effects of adding the pH-adjusting solution to the bivalirudin solution at a constant rate and under efficient mixing condition were studied. Multiple batches were generated by the same method.

The bivalirudin solution (~110 L) comprised bivalirudin at a concentration of 0.050 mg/ml dissolved in a 2.64% w/w mannitol solution. The pH-adjusting solution (~40 L) comprised 0.5 N sodium hydroxide in a 2.64% w/w mannitol solution.

The pH-adjusting solution was added to the bivalirudin solution at a controlled rate of 2 L/min using a peristaltic pump. A homogenizer was used to provide a high shear mixing environment (between about 1000 rpm and 1300 rpm) within the bivalirudin solution as the pH-adjusting solution was added, A feed tube extended from the peristaltic pump to an inlet in the homogenizer, so that the pH-adjusting solution was added to the bivalirudin solution at a site adjacent to the blades of the homogenizer. Simultaneously, a paddle mixer was used for mixing (mixing rate of between about 300 rpm and 700 rpm) near the surface of the bivalirudin solution. As the pH-adjusting solution was added, a small amount of material precipitated which later dissolved. After the pH-adjusting solution was completely added, the compounding solution was sterile filtered and lyophilized, and the lyophilizate was analyzed by HPLC for impurity levels.

In this study, which prepared 25 batches, analysis of impurity levels and reconstitution times for the lyophilizate are shown in Table 7.

TABLE 7

Characteristics of the batches generated by the compounding process that features addition of a pH-adjusting solution at a constant rate with efficient mixing.

|  | No. of batches | Mean ± SD | Maximum |
|---|---|---|---|
| $Asp^9$-bivalirudin (%) | 24 | 0.3 ± 0.1 | 0.6 |
| Total impurities (%) | 24 | 1.0 ± 0.4 | 2.0 |
| Largest unknown impurity (%) | 24 | 0.2 ± 0.1 | 0.3 |
| Reconstitution time (seconds) | 24 | 18 ± 6 | 42 |

The results of one batch was not included in the data presented in Table 7, as the method used to generate the batch was not compliant with the protocol established for this study.

Comparison of the batches of Example 5 to the batches of Example 4 revealed that the batches of Example 5 displayed significantly lower mean levels of $Asp^9$-bivalirudin, total impurities, and largest unknown impurity. The batches of Example 5 also showed smaller standard deviations relative to the means for levels of $Asp^9$-bivalirudin, total impurities, and largest unknown impurity. Together, these results suggest that the process demonstrated in Example 5 produced batches generally and consistently having lower levels of impurities than the process of Example 4.

In addition, the batches of Example 5 displayed significantly shorter mean reconstitution times, and smaller standard deviations relative to the mean, as compared to the batches of Example 4. These results suggest that the process of Example 5 generated batches generally and consistently having shorter reconstitution times than the batches generated by the process of Example 4.

A comparison between the batches generated in Example 4 and Example 5 is shown in Table 8 which assesses the mean values of the characteristics of the batches, and Table 9, which examines the maximum values of the characteristics of the batches:

TABLE 8

Comparison of mean values of the characteristics of the batches generated by the compounding process of Example 4 and the characteristics of the batches generated by the compounding process of Example 5 ($p < 0.05$).

|  | Batches of Example 4 Mean ± SD | Batches of Example 5 Mean ± SD | % change* | p |
|---|---|---|---|---|
| $Asp^9$-bivalirudin (%) | 0.5 ± 0.4 | 0.3 ± 0.1 | −40% | <0.0003 |
| Total impurities (%) | 1.4 ± 0.5 | 1.0 ± 0.4 | −29% | <0.004 |
| Largest unknown impurity (%) | 0.3 ± 0.1 | 0.2 ± 0.1 | −33% | 0.03 |
| Reconstitution time (seconds) | 30 ± 12 | 18 ± 6 | −40% | <0.000001 |

*% change = 100 × [(mean value from Example 5 batches) − (mean value from Example 4 batches)]/(mean value from Example 4 batches)

TABLE 9

Comparison of maximum values of the characteristics of the batches generated by the compounding process of Example 4 and the characteristics of the batches generated by the compounding process of Example 5 ($p < 0.05$).

|  | Batches of Example 4 Maximum | Batches of Example 5 Maximum | % change* |
|---|---|---|---|
| $Asp^9$-bivalirudin (%) | 3.6 | 0.6 | −83% |
| Total impurities (%) | 3.0 | 2.0 | −33% |
| Largest unknown impurity (%) | 0.5 | 0.3 | −40% |
| Reconstitution time (seconds) | 72 | 42 | −42% |

*% change = 100 × [(maximum value from Example 5 batches) − (maximum value from Example 4 batches)]/(maximum value from Example 4 batches)

As shown in Table 8, the levels of $Asp^9$-bivalirudin, total impurities, and largest unknown impurity, and the reconstitution time are all significantly less in the batches made by the process of Example 5 as compared to the batches made by the process of Example 4. Further, Table 9 shows that the maximum values for the levels of $Asp^9$-bivalirudin, total impurities, and largest unknown impurity, and the reconstitution time are also greatly less in the batches made by the process of Example 5 as compared to the batches made by the process of Example 4

Example 6

Generation of D-$Phe^{12}$-Bivalirudin in Stored Bivalirudin Pharmaceutical Formulations The bivalirudin pharmaceutical formulations prepared in Examples 1-3 were stored in refrigerated conditions and then evaluated by HPLC to compare the level of D-$Phe^{12}$-bivalirudin impurities among the different formulation methods. The results show that the levels of D-$Phe^{12}$-bivliarudin were similar across each formulation method, which indicated that the methods did not influence the generation of D-$Phe^{12}$-bivliarudin.

Having thus described in detail embodiments of the present invention, it is to be understood that the invention defined by the above paragraphs is not to be limited to particular details set forth in the above description as many apparent variations thereof are possible without departing from the spirit or scope of the present invention.

What is claimed is:

1. Pharmaceutical batches of a drug product comprising bivalirudin (SEQ ID NO: 1) and a pharmaceutically acceptable carrier for use as an anticoagulant in a subject in need thereof, wherein the batches have a pH adjusted by a base, said pH is about 5-6 when reconstituted in an aqueous solution for injection, and wherein the batches have a maximum impurity level of Asp$^9$-bivalirudin that does not exceed about 0.6% as measured by HPLC.

2. The pharmaceutical batches of claim 1, wherein the maximum impurity level of Asp$^9$-bivalirudin does not exceed about 0.4% as measured by HPLC.

3. The pharmaceutical batches of claim 2, wherein the maximum impurity level of Asp$^9$-bivalirudin does not exceed about 0.3% as measured by HPLC.

4. The pharmaceutical batches of claim 1, wherein the batches have a maximum total impurity level that does not exceed about 2% as measured by HPLC.

5. The pharmaceutical batches of claim 4, wherein the maximum total impurity level does not exceed about 1% as measured by HPLC.

6. The pharmaceutical batches of claim 5, wherein the maximum total impurity level does not exceed about 0.5% as measured by HPLC.

7. The pharmaceutical batches of claim 1, wherein the batches have a maximum level of D-Phe$^{12}$-bivalirudin that does not exceed about 2.5% as measured by HPLC.

8. The pharmaceutical batches of claim 1, wherein the pharmaceutically acceptable carrier comprises one or more of a bulking agent or a stabilizing agent.

9. The pharmaceutical batches of claim 8, wherein the bulking agent is a sugar.

10. The pharmaceutical batches of claim 9, wherein the sugar is mannitol.

11. Pharmaceutical batches of a drug product comprising bivalirudin (SEQ ID NO: 1) and a pharmaceutically acceptable carrier for use as an anticoagulant in a subject in need thereof, wherein the batches have a pH adjusted by a base, said pH is about 5-6 when reconstituted in an aqueous solution for injection, and wherein the batches have a maximum reconstitution time that does not exceed about 42 seconds and a maximum total impurity level that does not exceed about 2% as measured by HPLC.

12. The pharmaceutical batches of claim 11, wherein the maximum reconstitution time does not exceed about 30 seconds.

13. The pharmaceutical batches of claim 12, wherein the maximum reconstitution time does not exceed about 21 seconds.

14. The pharmaceutical batches of claim 11, wherein the pharmaceutically acceptable carrier comprises one or more of a bulking agent or a stabilizing agent.

15. The pharmaceutical batches of claim 14, wherein the bulking agent is a sugar.

16. The pharmaceutical batches of claim 15, wherein the sugar is mannitol.

17. The pharmaceutical batches of claim 1, wherein the base is sodium hydroxide.

18. The pharmaceutical batches of claim 11, wherein the base is sodium hydroxide.

19. Pharmaceutical batches of a drug product comprising bivalirudin (SEQ ID NO: 1) and mannitol for use as an anticoagulant in a subject in need thereof, wherein the batches have a pH adjusted by sodium hydroxide, said pH is about 5-6 when reconstituted in an aqueous solution for injection, and wherein the batches have a maximum reconstitution time that does not exceed about 42 seconds and a maximum total impurity level that does not exceed about 2% as measured by HPLC.

20. The pharmaceutical batches of claim 19, wherein the batches have a maximum impurity level of Asp$^9$-bivalirudin that does not exceed about 0.6% as measured by HPLC.

* * * * *

UNITED STATES PATENT AND TRADEMARK OFFICE
CERTIFICATE OF CORRECTION

PATENT NO. : 7,582,727 B1  Page 1 of 1
APPLICATION NO. : 12/180553
DATED : September 1, 2009
INVENTOR(S) : Gopal Krishna and Gary Musso It is certified that error appears in the above-identified patent and that said Letters Patent is hereby corrected as shown below:

ON THE TITLE PAGE

Item (73) Assignee: The "Medicinces" should read --Medicines-- Company, Parsippany, NJ (US)

Signed and Sealed this

Thirteenth Day of October, 2009

David J. Kappos
*Director of the United States Patent and Trademark Office*